United States Patent [19]

Kyung et al.

[11] 4,353,841

[45] Oct. 12, 1982

[54] AROMATIC ISOCYANATE PREPARATION

[75] Inventors: Jai H. Kyung, Dublin; Robert A. Grimm, Upper Arlington; Joseph G. Holehouse, Columbus, all of Ohio

[73] Assignee: Ashland Oil, Inc., Ashland, Ky.

[21] Appl. No.: 350,445

[22] Filed: Feb. 19, 1982

[51] Int. Cl.³ ............................................ C07C 118/00
[52] U.S. Cl. ................................................... 260/453 P
[58] Field of Search ...................................... 260/453 P

[56] References Cited

U.S. PATENT DOCUMENTS 4,174,377 11/1979 Trimble et al. .................... 423/365

OTHER PUBLICATIONS

Unland, J. Phys. Chem., vol. 77, 1952 (1973).

Primary Examiner—Dolph H. Torrence
Attorney, Agent, or Firm—William Kammerer

[57] ABSTRACT

An aromatic isocyanate is formed directly from an aromatic hydrocarbon, nitric oxide and carbon monoxide by contacting a Group VII or Group VIII metal catalyst at a temperature between 350° and 550° C. with a feed stream of said reactants.

8 Claims, No Drawings

AROMATIC ISOCYANATE PREPARATION

BACKGROUND OF THE INVENTION

1. Field of the Invention

This invention relates to a method for preparing an aromatic isocyanate.

2. Description of the Prior Art

Several methods have hitherto been developed for preparing aromatic isocyanates of which only one, however, has achieved commercial importance. Essentially all of such isocyanates of commerce are currently produced via the phosgenation of an aromatic amine. Since the appropriate amine must be first derived from the naturally occurring aromatic hydrocarbon, the overall reaction scheme is relatively complex from a processing standpoint. Also the manufacturing facility for implementing the method is capital intensive. In light of the high fixed costs involved in the current manufacture of these commodities, which are finding ever increasing industrial usages, the development of a more economical process is patently indicated.

The genesis of the approach to prepare isocyanates in accordance with the chemistry concerned herein is to be found in a number of related papers which began to appear in the early part of the last decade. One of the forerunners of these articles is Unland, M. L., J. Phys, Chem, 77, 1952 (1973). The latter reported work was directed to a study of the reductive removal of nitrogen oxides from automobile exhaust through the agency of a noble metal catalytic converter system. The most significant finding of this study was that carbon monoxide and nitric oxide combine at elevated temperatures to form a complexed isocyanate species on the surface of a noble metal catalyst.

The first potentially industrial application of the above finding is set forth in U.S. Pat. No. 4,174,377. Therein it taught that a variety of cyanate compounds including isocyanic acid can be prepared directly by contacting a noble metal hydrogenation catalyst at an elevated temperature with a feed stream of nitrogen oxide, carbon monoxide and a source of hydrogen. Although to date isocyanic acid has only limited industrial applications, the foregoing advance in the art nonetheless serves to conjure up the desideratum of preparing an aromatic isocyanate in such a chemically elegant manner.

SUMMARY OF THE INVENTION

In accordance with the present invention, a method is provided for preparing an aromatic isocyanate by the direct in situ formation thereof from an aromatic hydrocarbon, nitric oxide and carbon monoxide. The method comprises the vapor phase contacting of a Group VII or Group VIII metal catalyst at an elevated temperature with a feed stream consisting essentially of said reactants. Selectivity toward the formation of the isocyanate is governed by the mole ratio of nitric oxide to carbon monoxide present in the feed stream, same being maintained in the range of about 1–2. The concomitant mole ratio of carbon monoxide to the substrate feed is maintained between about 1 to 10.

DESCRIPTION OF THE PREFERRED EMBODIMENTS

The heterogeneous catalysts useful in the practice of this invention include the Group VII and Group VIII metals in a reduced activated form such as employed in conventional hydrogenation procedures. The preferred catalysts are the noble metals platinum and palladium. A representative Group VII metal is iridium. The indicated metal catalysts can be used in bulk or in a supported state. Various support materials are applicable for this purpose; however, γ-alumina is preferred. The preparation of a supported catalyst will be exemplified in the working examples given hereinbelow.

The reactants; viz., aromatic hydrocarbon, nitric oxide and carbon monoxide are introduced into a reaction sphere preferably consisting of a fixed bed of the catalyst wherein the temperature is maintained between about 350 and 550° C. The preferred temperature for carrying out the reaction is from 400°–500° C. The hydrocarbon substrate feedstock is desirably preheated along with an inert gas carrier where utilized; e.g., nitrogen, prior to the introduction of this feed component into the reaction sphere. The carbon monoxide and nitric oxide is desirably introduced directly into the reaction sphere without preheating. Pressure conditions applicable are essentially ambient with only moderately elevated pressures observed to maintain requisite flow rates of the component process feed streams.

The most critical relationship between the various reactant feeds is that which the nitric oxide bears to the carbon monoxide. This relationship on a molar basis is at least unity. The practical upper limit of nitric oxide to carbon monoxide is about two. Substantially higher excesses of the nitric oxide is prone to effect an intolerable degree of combustion of the substrate. The molar ratio of carbon monoxide to aromatic hydrocarbon substrate broadly ranges from 1–10. The preferred ratio is from about 1 to 4 on the same basis.

The working example set forth below illustrates the best mode developed for carrying out the invention utilizing benzene as the substrate. It will be noted that in this best mode embodiment the selectivity to benzonitrile is several fold greater than that of the selectivity to phenyl isocyanate realized. Notwithstanding the results obtained therein the process is nonetheless properly characterized as one for the preparation of the indicated isocyanate. This is so because under the reaction conditions utilized, contacting the catalyst with phenyl isocyanate per se results in the substantially complete conversion thereof to benzonitrile. Thus the contemplated invention clearly admits of being one for preparing an isocyanate. The suppression of the subsequent in situ conversion of the initially generated isocyanate to the corresponding nitrile derivative, on the other hand, represents a collateral aspect of the invention.

EXAMPLE I

Chloroplatinic acid in the amount of 3.33 g. was dissolved in 30 ml. water followed by the addition of 20 g. of 20–35 mesh γ-alumina. The resultant slurry was stirred gently to ensure a uniform coating of the metal compound on the alumina particles. Water was then removed in vacuo and the platinum coated alumina was calcined at 400° C. The calcination schedule consisted of 4 hours in vacuo; 1½ hours under 100 mm. pressure of oxygen; 30 minutes in vacuo; and finally 1 hour under 100 mm. hydrogen pressure. The resultant supported catalyst contained 8.1% by weight platinum metal.

The supported catalyst prepared as above in the amount of 8.6 g. was suspended in a suitable tubular reactor maintained at 500° C. Nitrogen at a rate of 220 ml./min. was initially passed through a preheater maintained at 180° C. and thence into the reactor. After the reactor temperature stabilized the benzene feed was introduced into the preheater along with indicated nitrogen flow rate, whereas nitric oxide and carbon monoxide were introduced directly into the reactor. The feed rates of nitric oxide, carbon monoxide and vaporized benzene were 78, 39 and 0.14 ml., respectively.

The reaction was conducted with the feed rates specified for a period of two hours resulting in a total benzene feed of 14.6 g. The run provided 15.8 g. of a liquid product containing a small amount of a white solid identified as ammonium carbonate. The product was analyzed by liquid-gas chromatography on OV-17 and Dexsil-400 columns. The analysis indicated the product to be composed of 0.2 wt. % phenyl isocyanate, 0.7 wt. % benzonitrile and the balance essentially benzene.

EXAMPLE II

An iridium catalyst supported on $\gamma$-alumina was prepared according to the procedure set forth in Example I. The calcined product contained 3% by weight iridium metal. The supported catalyst in the amount of 12 g. was contacted for 3 hours at 500° C. with feed streams of benzene, nitric oxide and carbon monoxide in the manner outlined in Example I while observing the respective feed rates noted therein. A total of 23.5 g. benzene was fed during the indicated period and a total of 10.3 g. of liquid product was collected. Chromatographic analysis of the product showed 0.1 wt. % phenyl isocyanate and 0.1 wt. % benzonitrile. Other reaction products identified included undefined polyaromatic hydrocarbons, carbon dioxide and ammonium carbonate.

We claim:

1. A method for preparing an aromatic isocyanate which comprises contacting a Group VII of a Group VIII metal catalyst at a temperature between about 350° and 550° C. with a feed stream consisting essentially of an aromatic hydrocarbon, nitric oxide and carbon monoxide wherein the mole ratio of nitric oxide to carbon monoxide is at least one and recovering aromatic isocyanate from the reaction effluent stream.

2. The method in accordance with claim 1 wherein the mole ratio of nitric oxide to carbon monoxide is from 1-2.

3. The method in accordance with claim 2 wherein the temperature is between 400° and 500° C.

4. The method in accordance with claim 3 wherein said aromatic hydrocarbon is benzene.

5. The method in accordance with claim 4 wherein the metal catalyst is platinum.

6. The method in accordance with claim 4 wherein the metal catalyst in iridium.

7. The method in accordance with claim 5 or 6 wherein the metal catalyst is supported.

8. The method in accordance with claim 7 wherein the support is $\gamma$-alumina.

* * * * *